(12) United States Patent
Katsuumi et al.

(10) Patent No.: US 6,174,165 B1
(45) Date of Patent: Jan. 16, 2001

(54) ENDODONTIC INSTRUMENT

(75) Inventors: Ichiroh Katsuumi, Tokyo; Kanji Matsutani, Tochigi-ken; Toshiyuki Takase, Tochigi-ken; Hideyuki Murai, Tochigi-ken, all of (JP)

(73) Assignee: Mani, Inc., Tochigi-ken (JP)

( * ) Notice: Under 35 U.S.C. 154(b), the term of this patent shall be extended for 0 days.

(21) Appl. No.: 09/372,073

(22) Filed: Aug. 11, 1999

(30) Foreign Application Priority Data

Sep. 11, 1998 (JP) .................................................. 10-257408

(51) Int. Cl.$^7$ ...................................................... A61C 5/02
(52) U.S. Cl. ......................................................... 433/102
(58) Field of Search ............................... 433/81, 102, 105, 433/165, 166, 224

(56) References Cited

U.S. PATENT DOCUMENTS

| 4,260,379 | * | 4/1981 | Groves et al. | 433/102 |
| 5,586,886 | * | 12/1996 | Roane | 433/102 |
| 5,762,497 | * | 6/1998 | Heath | 433/102 |
| 5,921,775 | * | 7/1999 | Buchanan | 433/102 |
| 5,980,250 | * | 11/1999 | McSpadden | 433/102 |
| 5,984,679 | * | 11/1999 | Farzin-Nia et al. | 433/102 |

* cited by examiner

Primary Examiner—Pedro Philogene
(74) Attorney, Agent, or Firm—Townsend & Banta

(57) ABSTRACT

Present invention relates to an endodontic instrument comprising a shaft and a work portion connecting to the shaft. The work portion has a plurality of helically extending blades to form a rectangular cross section in which the opposite edges of one set are longer edges and the opposite edges of the other set are shorter edges, the work portion having each apex of a right angle.

9 Claims, 5 Drawing Sheets

ENDODONTIC INSTRUMENT

BACKGROUND OF THE INVENTION

1. Field of the Invention

This invention relates to an endodontic instrument and, more particularly, to an instrument for treating a root canal such as a reamer, a file, or the like.

2. Description of Related Art

A root canal in a tooth is very narrow and has a delicately curved shape, which is individually deviated greatly. A reamer and a file are generally used as an endodontic instrument for grinding and shaping such a root canal. The reamer and the file are cutting devices having blades extending in a spiral shape, in which contour connecting the apex extending in a tapered shape. The reamer is mainly controlled to rotate to grind the root canals while the file is mainly controlled to be pushed to grind the root canals. Among such files, there are K files having relatively small twisting angles but capable of grinding by rotation and H files having the largest twisting angle used exclusively for grinding by pushing.

When a root canal therapy is made in use of, e.g., a file, a medical doctor grips the file by his fingers to grind and to shape the root canal by application of pushing and pulling control or slight rotating control. The doctor does therapeutic treatments without watching the area of the root canal ground by the file. Therefore, such treatments require skills and create various high level demands to performance and characteristics of files.

For example, as required characteristics for file, exemplified are to be able to flexibly follow curved shapes of root canals which are individually deviated greatly, to have good grinding property, to be able to easily remove the ground chips according to pushing and pulling control or rotating control, to have proper resistance responding to the canal shapes and instrument sizes, to have high breakdown angle property against torsional force, and so on. Some files have been proposed to satisfy such demands.

FIG. 5 is a diagram showing cross sections of some files commercially available. A circle shown in FIG. 5 is a circle with which the blades of the file at arbitrary positions are in contact. In the drawings, numeral 51 indicates a file having a square cross section and having a high cross-sectional secondary moment among the files commercially available. Therefore, the file provides high resistance against twisting and bending, but has a smaller rake angle (angle between the blade 51a and the circle), bad property of cutting and removal of cut chips, a lower traceability to a root canal.

Numeral 52 is a file having a triangle cross section and has a low cross-sectional secondary moment and a good traceability to a root canal. The blade 52a of the file has a large rake angle, and the file can have a large space within the circle, so that the file can have good property of cutting and removal of cut chips. However, the resistance against bending and twisting of a file is too low to transfer the force of the dentist to the blade as to cause a problem on the cutting capability, and also the blade may have slightly inferior durability. Numeral 53 is a file having a rhomb cross section, which has good property of cutting and removal of cut chips and has a proper resistance against bending and twisting because the file has a wider rake angle of the blade 53a than that of the file 51 having a square cross section to create a large space within the circle. Accordingly, the file can be used preferably for grinding the root canals.

The file in the rhomb cross section is not free from suffering some problem, and the durability as a blade in cutting work and the balance in proper flexibility and, conversely, proper rigidity and high cutting capability are still unsatisfactory. Moreover, forming such files into an accurate rhomb shape brings high costs to render the products expensive.

SUMMARY OF THE INVENTION

It is an object of the invention to provide an endodontic instrument, having good cutting capability, good removing capability for cutting chips, proper rigidity in bending and twisting, and proper flexibility in tracing a root canal, and rendering the costs reduced.

The endodontic instrument according to the invention includes a shaft, and a work portion connecting to the shaft and having a plurality of helically extending blades to form a rectangular cross section in which the opposite edges of one set are longer edges and the opposite edges of the other set are shorter edges, the work portion having each apex of a right angle.

With such an endodontic instrument according to the invention, the work portion having a rectangular cross section makes the rake angle of the blade larger and space formed in front of the blade larger. Therefore, the endodontic instrument can improve the cutting capability and surely, easily remove cut chips.

Since the cross section of the work portion is in a rectangular shape, the fabrication of the cross section is no different from that for a K file having a square cross section. Therefore, the production cost does not increase, and the endodontic instrument can be made inexpensively.

The endodontic instrument for root canal therapy (hereinafter referred to as simply, "endodontic instrument"), since having a rectangular cross section at the work piece, has entirely different values in cross-sectional secondary moments in a direction along the longer edge and in a direction along the shorter edge. Consequently, the work portion may have an orientation preference in terms of the curving easiness at an arbitrary section in an axial direction. However, since the work portion is formed in a helically extending shape having the rectangular cross section, the work portion as a whole does not have such an orientation preference in the curving easiness, so that the endodontic instrument can provide flexibility and rigidity with a higher lever for treatments of root canals.

BRIEF DESCRIPTION OF THE DRAWINGS

The above and other objects and features of the invention are apparent to those skilled in the art from the following preferred embodiments thereof when considered in conjunction with the accompanied drawings, in which:

FIG. 1(a), is an endodontic instrument according to a preferred embodiment of the invention wherein FIG. 1(a) is a front view of the endodontic instrument;

DESCRIPTION OF PREFERRED EMBODIMENTS

Figure 1A:
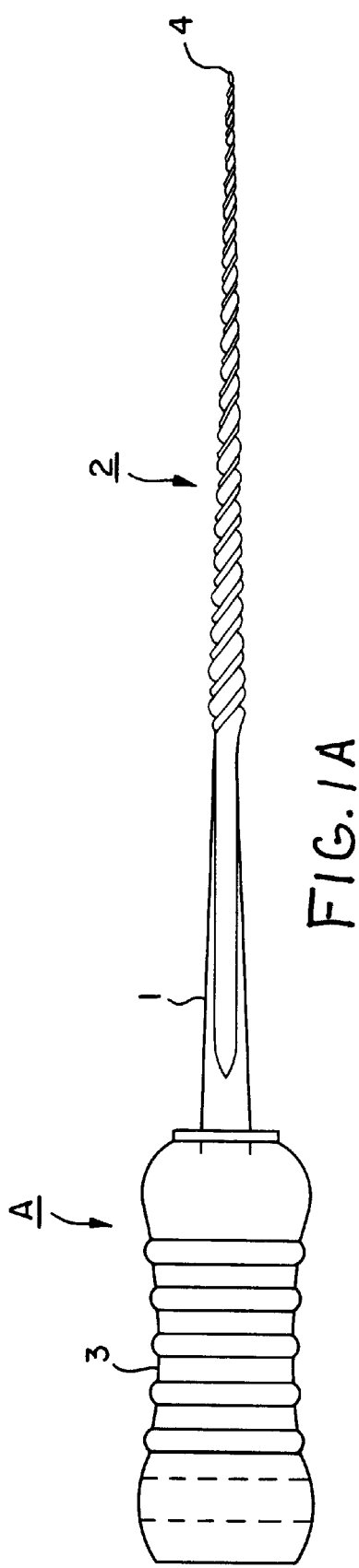
Figure 1B:
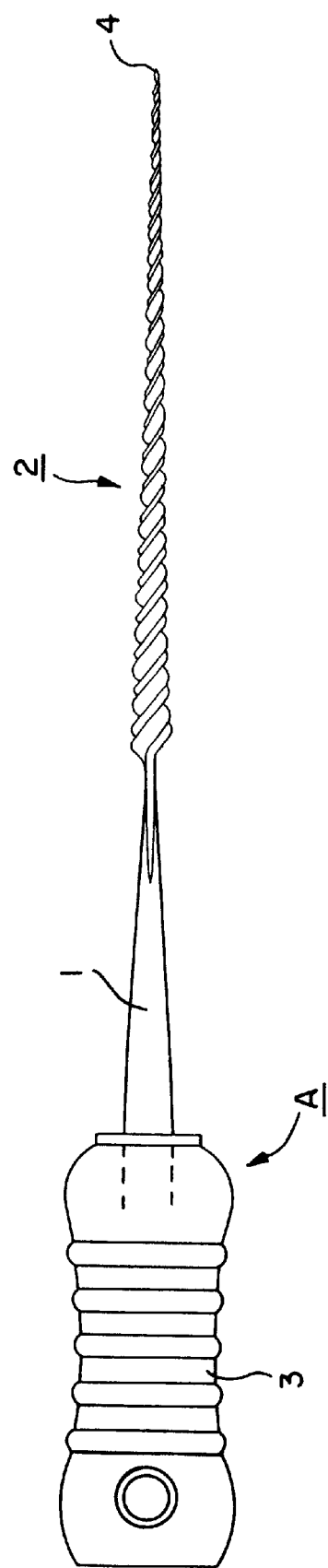
FIG. 1(b) is a side view of the endodontic instrument shown in FIG. 1(a)
Figures 2, 3:
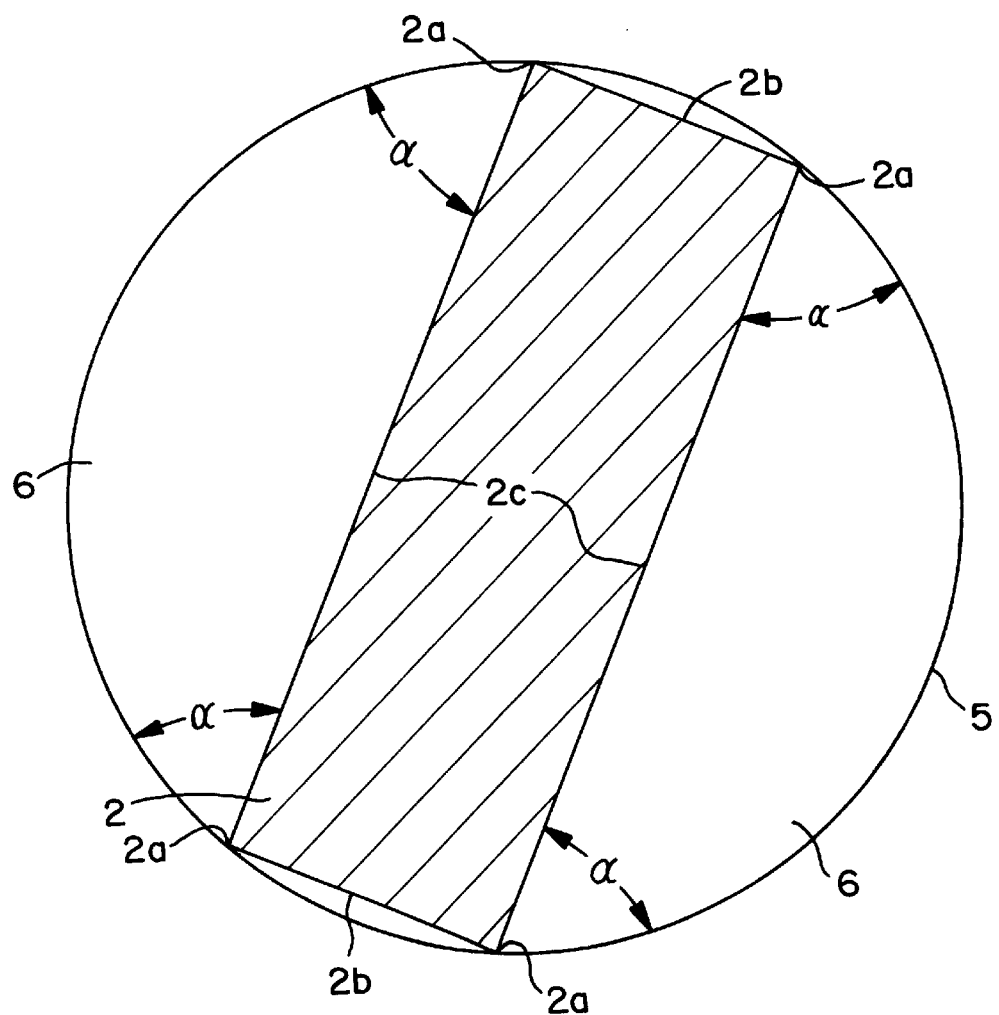
FIG. 2 is an enlarged view showing a tip portion of a work portion.
FIG. 3 is an illustration showing a cross section of the work portion.
Figure 4:
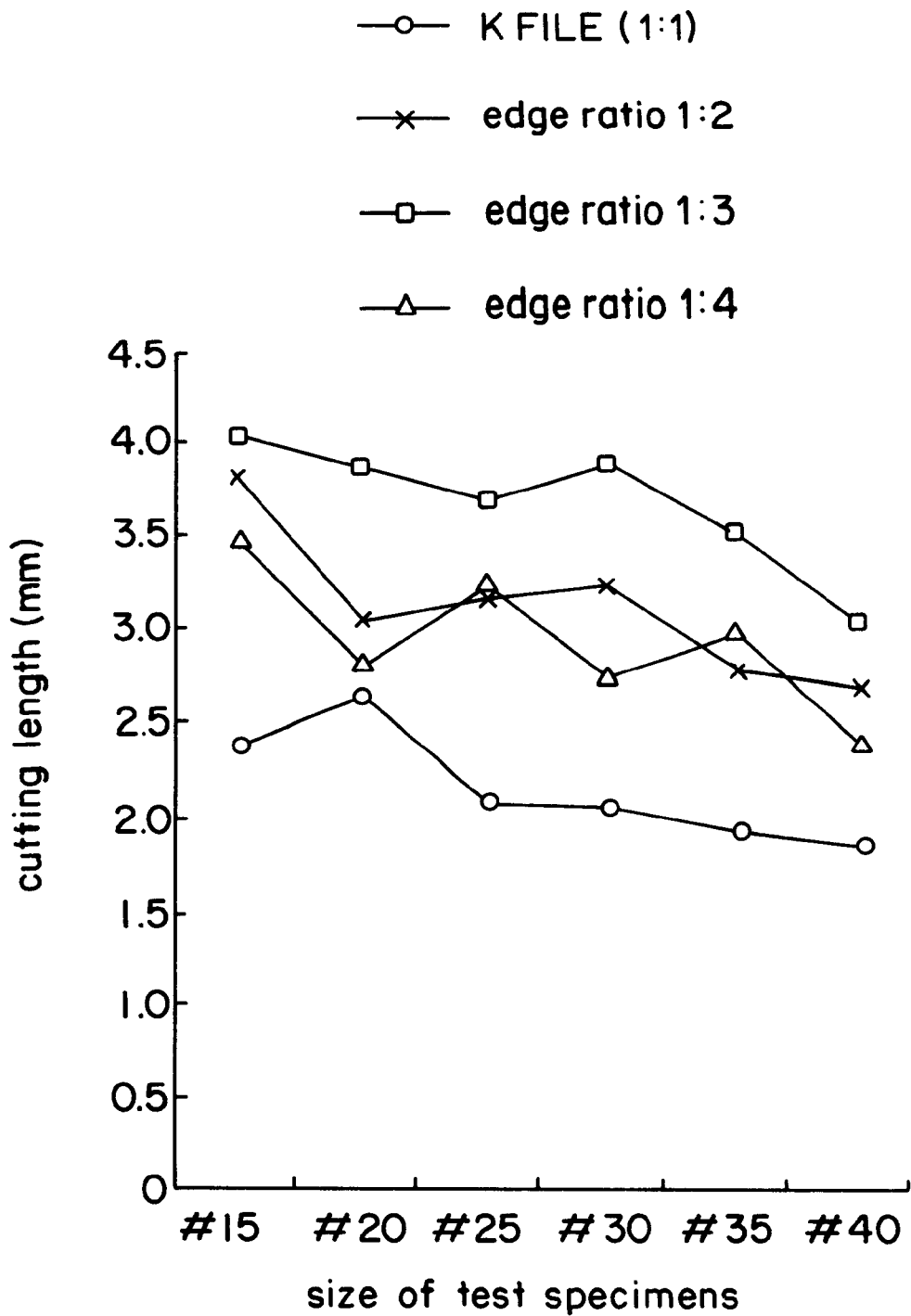
FIG. 4 is a diagram showing comparing results of endodontic instruments according to the embodiment and a conventional K files.
Figure 5:
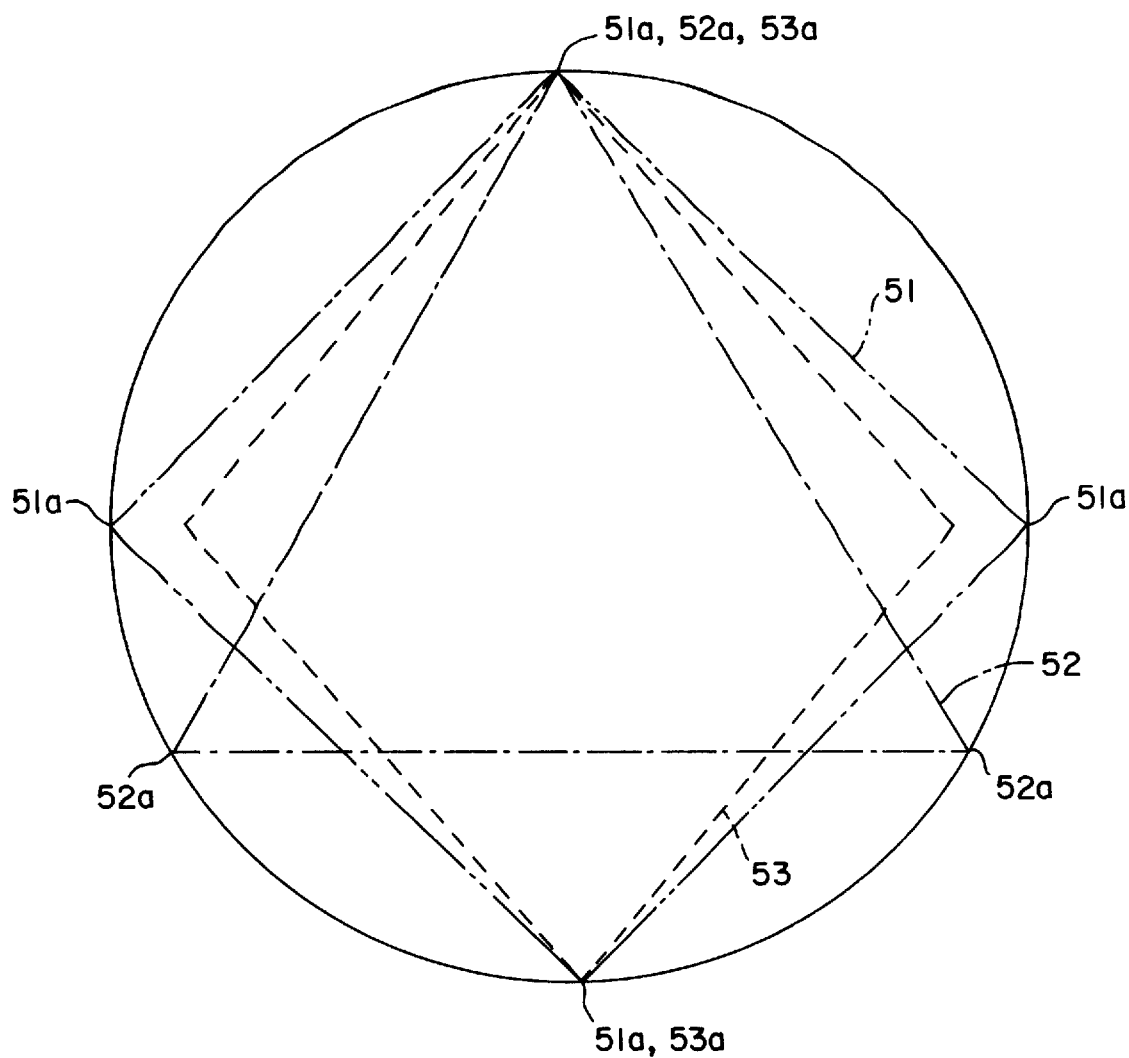
FIG. 5 is a diagram showing cross section of conventional endodontic instruments.

Referring to the drawings, endodontic instruments according to preferred embodiments of the invention are described. FIGS. 1(a), 1(b) are illustrations of an endodontic instrument according to a preferred embodiment of the invention wherein FIG. 1(a) is a front view of the endodontic instrument and FIG. 1(b) is a side view of the endodontic instrument; FIG. 2 is an enlarged view showing a tip portion of a work portion; FIG. 3 is an illustration showing a cross section of the work portion; and FIG. 4 is a diagram showing comparing results of endodontic instruments according to the embodiment and a conventional K files.

The endodontic instrument A is a tool for shaping a root canal by grinding the canal. The endodontic instrument A is provided with variations having plural diameters in a range of No. 6 in size (the thickness of a distal end is 0.06 mm) to No. 140 in size (the thickness of a distal end is 1.40 mm). This endodontic instrument is used for shaping root canals by grinding the canals upon controlling the endodontic instrument by clamping the endodontic instrument with dentist's finger tips in reliance with slight feeling on the instrument. According to this control, the dentist changes the endodontic instrument to another instrument having a larger diameter as the ground canal getting a larger diameter and controls the endodontic instrument to shape the canal so that the root canal has the diameter and shape as targeted.

The endodontic instrument A is constituted of a shaft portion 1 and a work portion 2 connecting to the shaft 1. In this embodiment, a handle 3 is formed in a united body with the shaft 1 to be clamped by fingers of an operating dentist. A tip 4 of the work portion 2 is constituted as an apex portion having a prescribed angle (e.g., 60 to 90 degrees) as shown in FIG. 2 notwithstanding the size and the cross-sectional shape of the work portion 2.

The shaft 1 is formed in a straight shape or tapered shape and formed by an insertion molding into the handle 3 during the series of manufacturing processes as to form a united body. But as an instrument for dental treatment, the handle is not necessarily molded as a united body on the shaft, and for example, the shaft may be constituted with a predetermined handle that can be attached to a chuck of an air tool or the like, or the endodontic instrument may be formed without any handle as to be attached to a tool not requiring a handle. In any event, as an instrument for dental treatment, the invented endodontic instrument is not limited to an endodontic instrument manipulated by hands of a dentist as in this embodiment.

The shaft 1 is formed into a circle shape and gradually into a rectangular shape of the cross section of the work piece 2 as coming closer to the work portion 2 from the end of the handle 3. The shaft 1 thus structured does not change the cross-sectional shape and area abruptly, so that the instrument can respond in a good way to bending force exerting during treatments in eliminating concentrations of stresses. The longer edge direction of the rectangular has a higher rigidity while the shorter edge direction of the rectangular has an excellent flexibility, so that the endodontic instrument can help inputs of force and touching feelings of the dentist when, particularly, a molar is treated around which fingers are not readily placed by manipulating the instrument back and forth after selecting an edge between the longer edge and the shorter edge upon rotating the instrument according to curving directions of the treated root canal.

The work portion 2, as shown in FIG. 3, has a rectangular cross section when cut in a perpendicular direction to the longitudinal direction of the shaft 1, and is screwed as to form a helical shape with a prescribed lead or leads. The envelope of respective blades 2a having a prescribed pitch or pitches are in a tapered form. The work portion 2 is not necessarily in a simple tapered form from the shaft 1 to the tip 4, and the work portion 2 may be formed in a form that a middle portion of the work portion 2 has a larger diameter and the work portion 2 is in a tapered form from the middle portion to the shaft 1 and the tip 4 as well or the work portion 2 is in a straight form from the middle portion to the shaft 1.

That is, the work portion 2 is formed by screwing, into a helical form, an intermediate material having the rectangular cross section whose the ratio of the shorter edge 2b to the longer edge 2c is predetermined and whose area is reduced as coming closer to the tip 4 from the shaft 1. Therefore, when a root canal is treated, and when the work portion 2 is moved in an axial direction by moving the work portion 2 back and forth, the blades 2a seemingly rotate along the circumference of a circle 5 shown in FIG. 4 as proceeding according to the leads, and the root canal can be cut by this rotational movement. Particularly, the work portion 2 can take a large rake angle α formed by an angle between the blade 2a and the circle 5, so that the work portion can obtain good cutting or grinding property.

The work portion 2 also can create a large space 6 between the cross section of the work portion 2 and the circle 5. Therefore, chips cut by the blades 2a according to the pushing and pulling movements of the work portion 2 enter in the space 6 and are discarded outside through the space 6. At that time, since the space 6 has a large space, the cut chips can be easily and surely removed.

The ratio of the shorter edge 2b to the longer edge 2c constituting the edges of the rectangular cross section is not specifically limited, and when the ratio between both edges 2b, 2c is changed, good cutting capability can be realized. However, if the ratio of the edges becomes too large, the cutting capability may be improved but losses resistance against bending movements, and resistance against twisting as well.

The manufacturing method for realizing the rectangular cross section of the work portion 2 thus described is not limited specifically. That is, the rectangular cross section can be formed by grinding a material having a tapered shape in advance or by pressing and grinding such a material. Such a method is substantially the same as the method for producing a K file having a square cross section, and an inexpensive endodontic instrument A can be provided in reducing the manufacturing costs by forming the work portion 2 with such simple fabrication processes.

The inventors of this invention implemented some experiments regarding cutting capability, resistance against bending, and resistance against twisting in producing test specimens having the edge ratio of the shorter edge to the longer edge of 1:2 to 1:4. Those were also compared with the K file having a square cross section in which two edge ratio is of 1:1.

The experiment results regarding the cutting capability is shown in FIG. 4. First, the test specimens were so formed that endodontic instruments with respect to the edge ratios have sizes between No. 15 (the diameter of the proximal portion of the tip 4 is 0.15 mm) and No. 40 (the diameter of the proximal portion of the tip 4 is 0.40 mm), and each size had five specimens, which were measured by a cutting capability testing apparatus in which a length in an acrylic plate, cut by reciprocal movements of 300 times, 60 times per minute, with strokes under a prescribed weight load, was measured. The results were that the edge ratio of 1:3 had the best cutting capability among the entire sizes, and the instruments having edge ratio of 1:2 and 1:4 indicated the same cutting capability. However, regardless the edge ratio, the endodontic instruments according to the invention had better cutting capability than that of the K file having the square cross section.

The experiments regarding resistance against bending were implemented in use of an exclusive bending test apparatus in which maximum torque was measured where a 3-mm tip of the test specimens was immobilized and where a jig for bending was rotated for 45 degrees, under the conditions same as the above cutting capability experiments with respect to the size and sample number of the test specimens. In these experiments, the K file having the square cross section which was the largest cross-sectional area indicated the strongest result, and as the edge ratio became larger, the result became weaker. This result can be said as a matter of course because the shorter edge size became shorter as the edge ratio became larger where the longer edge keeps a constant size since the diameter of the respective sizes was defined by the proximal end of the tip 4, and because the cross section became smaller as the edge ratio became larger.

The experiments regarding resistance against twisting were implemented in use of an exclusive twisting test apparatus in which maximum torque and rotation angle speed at a time that the specimen was broken down were measured where a 3-mm tip and a portion located 17 mm from the tip of the test specimens were immobilized to a jig and where the jig on a proximal end was rotated to twist the specimen, under the conditions same as the above cutting capability experiments with respect to the size and sample number of the test specimens. In this experiment, the K file having the square cross section demonstrated a certain resistance against twisting notwithstanding of changes of the sizes, but the test specimen of the edge ratio of 1:4, though having some deviations, indicated, as a trend, a certain resistance against twisting notwithstanding of changes of the sizes and had a larger breakdown angle than that of the K file having the square cross section. The test specimen having the edge ratio of 1:3 indicated the resistance against twisting substantially equivalent to the K file having the square cross section.

From the experiment results, it can be inferred that an edge ratio of the rectangular capable of obtaining good cutting capability and producing strength practically raising no problem is in a range of 1:1.5 as a lower limitation and 1:5 as an upper limitation.

It was turned out that the strength against bending became smaller as the edge ratio became larger according to the results of the experiment. This indicates that if the edge ratio becomes larger the flexibility is improved though the instrument loses its strength.

From the experiment results, the capability of the endodontic instrument A according to this embodiment was compared with the capability of the conventional endodontic instrument having a rhomb shaped cross section. As a result, the endodontic instrument A had a good durability since having a blade 2a of 90 degrees, a large angle. Though the endodontic instrument having the rhomb shape is in contact with the cutting surface of the root canal at two points, the endodontic instrument A is in contact with the surface at four points (two points are for blades, and the other two points are for support), and where those are utilized effectively, the endodontic instrument according to the embodiment can bring a higher cutting capability than that of the cutting capability of the endodontic instrument having a rhomb cross section.

Where the work portion 2 constituting the endodontic instrument A is formed with a rectangular cross section having a constant edge ratio in the longitudinal direction (axial direction), the work portion 2 can provide substantially the same flexibility as proportioned to the increase of the diameter over the whole length. However, it may be preferable that the work portion 2 has flexibility different in the longitudinal direction depending on the cases where the root canal to be treated has a complicated shape and on the sizes.

According to the experiment results, the edge ratio of the work portion 2 may be changed in a longitudinal direction (the axial direction) to provide a different flexibility at a prescribed section by forming the portion with a rectangular cross section having a different edge ratio.

That is, an endodontic instrument A having a smaller size number may hardly obtain good cutting capability because of the flexibility from a very fine diameter of the tip of the work portion 2. In such a case, for example, where the edge ratio of the rectangular cross section of the work portion 2 on a side of the shaft 1 is set larger, and where the edge ratio of the rectangular cross section of the work portion 2 on a side of the tip 4 is set smaller, it is possible to form the endodontic instrument with more flexibility on a side of the shaft 1 and with improved cutting capability on a side of the tip 4 as well as improved resistance against bending on a side of the tip 4. Such an endodontic instrument A is more advantageous when the shape of the root canal is further complicated.

Such variations about the edge ratio of the work portion 2 thus described are applicable to a single section or plural sections of the work portion 2 according to the target, and the edge ratio can be changed gradually across the entire sections or be changed greatly at a single section. An intermediate portion may be changed while the work portion 2 keeps the same edge ratio on the sides of the shaft 1 and the tip 4.

The material constituting the endodontic instrument A is not specifically limited. Generally, a stainless steel is used. When a stainless steel is used, an austenite stainless steel free from occurrence of rust is preferably used, and also, the material may be preferably drawn into a material having a fiber organization. Where the material has such a fiber organization across the whole length, resistances against bending and twisting can be improved.

A shape memory alloy may be used for a material for the endodontic instrument A. In such a case, it is preferable to use the material in a range of superelasticity by thermally treating the shape memory alloy in a prescribed manner in advance.

Although in the above embodiments, the endodontic instrument, in which the handle 3 is attached to the shaft 1 and the work portion 2, to be manipulated by dentist's fingers, the endodontic instrument according to this invention is not limited to this, and for example, the invented endodontic instrument may be used for a motor tool where a joint for connecting to the motor tool is provided in lieu of the handle 3.

Figure 6:
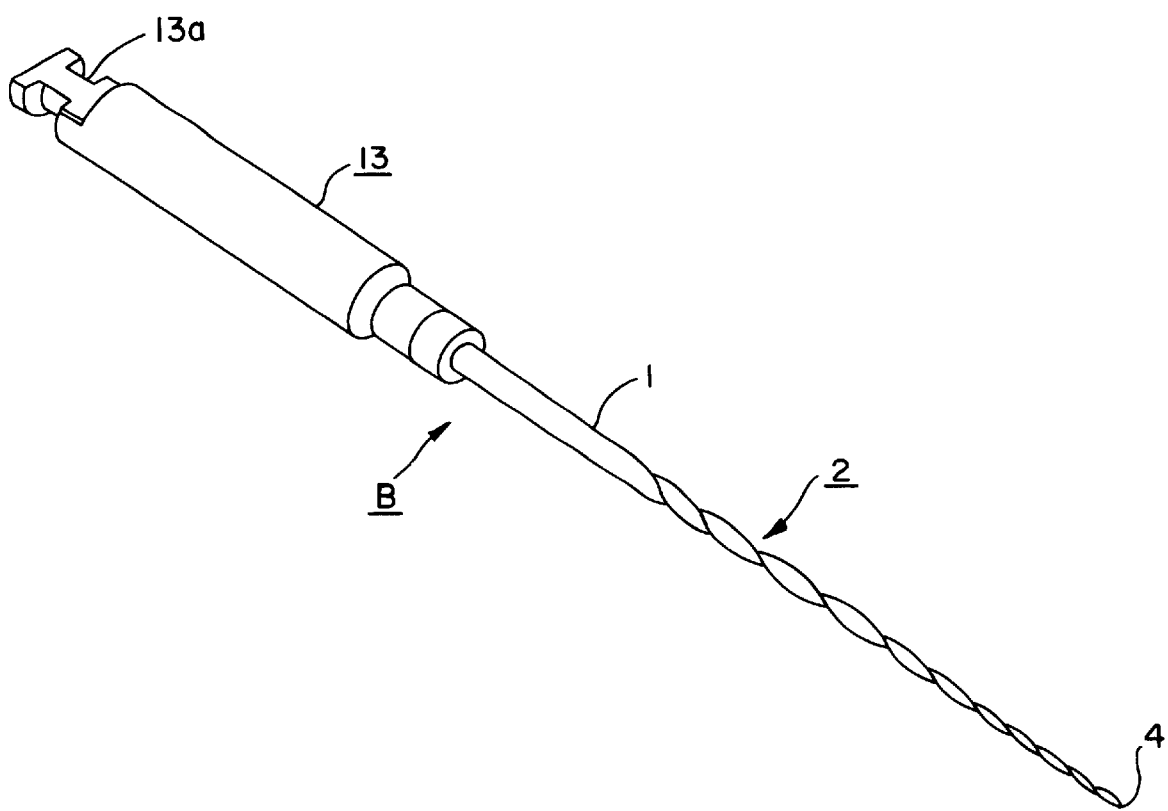
FIG. 6 is a perspective view showing an endodontic instrument according to a second embodiment of the invention.

FIG. 6 is a perspective view showing an endodontic instrument B according to the second embodiment of the invention. The endodontic instrument B according to the second embodiment is used for an attachment member for a motor tool. The shaft 1 and the work portion 2 are the same as those in the first embodiment, but a joint grip 13 is attached to a proximal end of the shaft 1. One end of the joint grip 13 is inserted in a joint hole, not shown, for the motor tool, and the joint grip 13 has a meshing portion 13a for receiving motion power.

The endodontic instruments according to this invention, in addition to the endodontic instrument to be manipulated by dentist's fingers, can be provided as endodontic instruments for a motor tool likewise the endodontic instrument B according to the second embodiment.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention should not be limited by the specification, but be defined claims set forth below.

What is claimed is:

1. An endodontic instrument comprising:
    a shaft; and
    a work portion connecting to the shaft and having a plurality of helically extending blades to form a rectangular cross section in which the opposite edges of one set are longer edges and the opposite edges of the other set are shorter edges, the work portion having each apex of a right angle
    wherein a ratio of the shorter edge to the longer edge of the rectangular cross section is between 1 to 2 and 1 to 4.

2. The endodontic instrument according to claim 1, wherein the proximal end of the shaft is attached to a handle.

3. The endodontic instrument according to claim 1, wherein the base portion of the shaft is attached to a joint of a motor tool.

4. An endodontic instrument comprising:
    a shaft having a proximal end and a second end;
    a work portion having a first end connecting to the proximal end of the shaft, a middle portion and a second end, said work portion having a plurality of helically extending blades to form a rectangular cross section, the opposite edges of the one set of blades having longer edges, the opposite edges of the other set of blades having shorter edges, each apex of blades forming a right angle, a ratio of the shorter edge to the longer edge of the rectangular cross section being between 1 to 2 and 1 to 4, the work portion creating a large rake angle so that chips cut by the blades are easily discarded through a large space formed by said work portion when cutting; and
    a tip formed at the second end of said work portion.

5. The endodontic instrument of claim 4, wherein said work portion is tapered from the shaft to the tip.

6. The endodontic instrument of claim 4, wherein the middle portion of said work portion has a diameter larger than the first and second end of said work portion.

7. The endodontic instrument of claim 4, wherein the work portion is in a straight form from the shaft to the middle portion.

8. The endodontic instrument of claim 4, further comprising a joint grip attached to a proximal end of the shaft, said joint grip comprising a meshing portion for receiving motion power.

9. The endodontic instrument of claim 4, wherein the proximal end of the shaft is attached to the handle.

\* \* \* \* \*